(12) United States Patent
Oshita et al.

(10) Patent No.: US 7,052,724 B2
(45) Date of Patent: May 30, 2006

(54) METHOD OF PRODUCING ACTIVE DRY YEAST

(75) Inventors: Katsumi Oshita, Osaka (JP); Nobuyuki Fukui, Osaka (JP); Hideko Yomo, Osaka (JP); Yusuke Umezawa, Osaka (JP)

(73) Assignee: Suntory Limited, Osaka (JP)

( * ) Notice: Subject to any disclaimer, the term of this patent is extended or adjusted under 35 U.S.C. 154(b) by 0 days.

(21) Appl. No.: 10/239,761

(22) PCT Filed: Jan. 31, 2002

(86) PCT No.: PCT/JP02/00766

§ 371 (c)(1),
(2), (4) Date: Dec. 30, 2002

(87) PCT Pub. No.: WO02/062966

PCT Pub. Date: Aug. 15, 2002

(65) Prior Publication Data

US 2004/0018274 A1    Jan. 29, 2004

(30) Foreign Application Priority Data

Feb. 2, 2001    (JP)    ............................. 2001-026649

(51) Int. Cl.
*C12N 1/04* (2006.01)
*C12N 1/18* (2006.01)
*C12C 11/00* (2006.01)
*C12G 1/00* (2006.01)

(52) U.S. Cl. ..................... 426/62; 426/11; 426/592; 435/255.21

(58) Field of Classification Search ............... 426/11, 426/16, 29, 62, 592; 435/93, 245, 255.2, 435/255.21, 255.1
See application file for complete search history.

(56) References Cited

U.S. PATENT DOCUMENTS

| | | | | |
|---|---|---|---|---|
| 4,370,420 A | * | 1/1983 | Clement et al. | ......... 435/255.2 |
| 5,627,062 A | * | 5/1997 | Divies et al. | ............... 435/178 |
| 5,693,788 A | * | 12/1997 | Mandai et al. | ......... 536/123.13 |
| 5,702,943 A | * | 12/1997 | Ehret | ....................... 435/253.6 |
| 6,159,725 A | * | 12/2000 | Klaassen et al. | ....... 435/254.21 |
| 6,232,111 B1 | * | 5/2001 | Zhang et al. | ........... 435/254.21 |
| 6,468,782 B1 | * | 10/2002 | Tunnacliffe et al. | ........ 435/260 |
| 6,593,469 B1 | * | 7/2003 | Barresi et al. | .............. 536/112 |

FOREIGN PATENT DOCUMENTS

JP    2002-95465    4/2002

OTHER PUBLICATIONS

Boulton et al. Principles and Practices of Winemaking. 1996, Chapman & Hall (Publ.), pp. 123-124.*
Papazian, C. The New Complete Joy of Home Brewing. 1991, Avon Books, p. 82.*
Salek et al., Trehalose-stabilisation of osmophilicity and viability of baker's and distiller's yeast: applications to storage and drying. Chem. Mikrobiol. Technol. Lebensm., vol. 17, No. 1/2 p 14-21, (1995).
Ganthala et al. Xerotolerance in fission yeasts and the role of glycerol as compatible solute. Arch. Microbiol., vol. 162, No. 1/2 p 108-113, (1994).
Gadd, G.M. et al. "The role of trehalose in dehydration resistance of Saccharomyces Cerevisiae", FEMS Microbiology Letters, 48 (1987) pp 249-254.
Mansure, J.J.C. et al. "Trehalose inhibits ethanol effects on intact yeast cells and liposomes", Biochimica et Biophysica Acta 1191 (1994) pp 309-316.

* cited by examiner

*Primary Examiner*—Keith Hendricks
(74) *Attorney, Agent, or Firm*—Paul E. White, Jr.; Manelli Denison & Selter PLLC

(57) ABSTRACT

A novel technique is provided for drying a yeast for brewing and a method of producing alcoholic beverages by using the yeast. It is intended to provide a method of producing a dry yeast which has the optimum fermentability when directly used in fermentation and gives an appropriate flavor without needing prepropagation, and a method of producing alcoholic beverages by using the yeast.

A method comprising incorporating a stabilizer such as trehalose into a yeast which has been recovered from the fermentation step, and, if desired, further incorporating glycerol into the yeast to thereby lower the water activity in the cells, and then dehydrating/drying the yeast while sustaining a high viable cell ratio and favorable fermentability; and alcoholic beverages produced by using the yeast.

13 Claims, 9 Drawing Sheets

● : Initial trehalose content 10%(w/w), treated at 10 °C
○ : Initial trehalose content 10%(w/w), treated at 20 °C
▲ : Initial trehalose content 5%(w/w), treated at 10 °C
△ : Initial trehalose content 5%(w/w), treated at 20 °C ● : Initial trehalose content 10%(w/w), treated at 10 °C
○ : Initial trehalose content 10%(w/w), treated at 20 °C
▲ : Initial trehalose content 5%(w/w), treated at 10 °C
△ : Initial trehalose content 5%(w/w), treated at 20 °C ● : Initial trehalose content 10%(w/w), treated at 10 °C
○ : Initial trehalose content 10%(w/w), treated at 20 °C
▲ : Initial trehalose content 5%(w/w), treated at 10 °C
△ : Initial trehalose content 5%(w/w), treated at 20 °C
■ : Initial trehalose content 0%(w/w), treated at 10 °C
□ : Initial trehalose content 0%(w/w), treated at 20 °C ● : Trehalose-treatment
○ : Water-treatment ●: Trehalose-treatment ○: Water-treatment

A

B

●: Trehalose-treatment
○: Water-treatment

A

B

● : Trehalose-treatment
○ : Water-treatment

● : Recovered yeast
△ : Dry yeast
■ : Marketed dry yeast

METHOD OF PRODUCING ACTIVE DRY YEAST

This application is the national phase of international application PCT/JP02/00766, filed Jan. 31, 2001, which designated the U.S.

TECHNICAL FIELD TO WHICH THE INVENTION BELONGS

This invention relates to a method of producing an active dry yeast having high fermentability which comprises incorporating a stabilizer such as trehalose into a yeast, which has been recovered from the fermentation step, to enhance the resistance to dryness and then drying the yeast at a low temperature; a method of producing alcoholic beverages by using the active dry yeast; and alcoholic beverages obtained by the production method.

PRIOR ART

When yeasts recovered from the fermentation step in producing alcoholic beverages are stored alive, their activity namely, fermentability, gradually decreases. Therefore, use of such a yeast, which has been stored for a long period of time, as a starter in producing alcoholic beverages may cause fermentation failure or have a deleterious effect on the characteristics alcoholic beverages obtained. In view of this problem, there have been developed methods for storing recovered yeasts which their activity to be maintained. However, no really practical or satisfactory method has been developed so far. JP(Kokai) Hei-8-266297 discloses a method of measuring the activity and fermentability of a yeast and thus evaluating its suitability as a starter.

Drying may be cited as an example of means of storing yeasts while maintaining their activity. Dry baker's yeast glycerol to a pressed yeast to improve the moisture-retaining properties and then drying the yeast.

When dry yeasts are employed as yeasts for producing alcoholic beverages, there arises another problem. Dry yeasts are made of yeasts having been aerobically cultured as a starting material to increase the yeast cell yield.

In yeast having been aerobically cultured, an aerobic metabolic system of the yeast is accelerated while an anaerobic metabolic system required in alcohol fermentation is inhibited. Thus, dry yeasts prepared from aerobically cultured yeasts have lowered fermentability. Therefore, it is known that when these dry yeasts are used as starters in producing alcoholic beverages, the yeasts exert undesirable effects (for example, a decrease in the flavor components) on the qualities of the alcoholic beverages. In actuality, alcoholic beverages produced by using dry yeasts prepared from yeasts having been aerobically cultured contain few esters and thus have organoleptically unfavorable qualities. When these dry yeasts prepared from yeasts having been aerobically cultured are used as starters, sulfur dioxide is formed only in a small amount during fermentation and, as a result, the stability of the flavor of the thus obtained alcoholic beverages is lowered, compared with a case where yeasts having been anaerobically cultured are used as starters.

When dry yeasts are employed as yeasts for producing alcoholic beverages, there arises still another problem. It has been practically used blackstrap molasses as a medium for culturing yeasts serving as the starting materials of dry yeasts. However, dry yeasts prepared from yeasts which have been cultured with the use of blackstrap molasses as the medium are not favorable as starters. Blackstrap molasses contains sucrose as a sugar component which is digested into glucose and fructose by sucrase occurring in the cell wall surface layer of yeasts. It is known that glucose inhibits the metabolic system of maltose which is the main sugar component of wort (i.e., so-called glucose repression). There is therefore a concern that when a dry yeast prepared from a yeast having been cultured in a blackstrap molasses medium is used as a starter in producing alcoholic beverages made from wort (beer, whisky, etc.), the maltose metabolic system will be repressed and thus fermentation failure will occur. To use these conventional dry yeasts as starters, the dry yeasts should be cultured in wort under anaerobic conditions and thus equipment for culturing the starters is required.

On the other hand, trehalose, which is a nonreducing disaccharide composed of two D-glucose molecules bonded to each other via a 1,1-bond, is contained in a large amount in fungus and yeasts. It is well known that intracellular trehalose increases in yeast resistance to drying and freezing. It has been disclosed that when a yeast having a high trehalose content in its cells is freeze-dried or a yeast is freeze-dried in a trehalose solution with a high concentration, the survival ratio of the yeast is elevated (FEMS Microbiology Letters, 48(1987), 249–254). Biosynthesis of trehalose in yeasts is induced by a heat shock. Based on this phenomenon, there has been disclosed a method of producing a dry yeast wherein the culture temperature is elevated at the final stage of culturing a yeast serving as the starting material of the dry yeast to thereby induce biosynthesis of trehalose. Thus, the trehalose content in the yeast cells can be elevated and, as a result, resistance to drying of the yeast can be improved (FEBS Let., 220, 113–115 (1987)). However, the biosynthesis of trehalose is strongly induced under aerobic culture conditions. Accordingly, it is seemingly impossible to strongly induce the biosynthesis of trehalose and elevate the trehalose content in yeasts to thereby improve the resistance to drying in the case of dry yeasts for brewing, since it is important from a viewpoint of serving as starters that the anaerobic metabolic has been accelerated in these yeasts.

Problems that the Invention is to Solve

The present invention provides a method of producing an active dry yeast which shows high fermentability in producing alcoholic beverages and thus makes it possible to produce alcoholic beverages having excellent flavor characteristics without the need for a starter culture; a method of producing alcoholic beverages by using this active dry yeast; and alcoholic beverages having an excellent flavor produced by this method.

DETAILED DESCRIPTION

Figure 1:
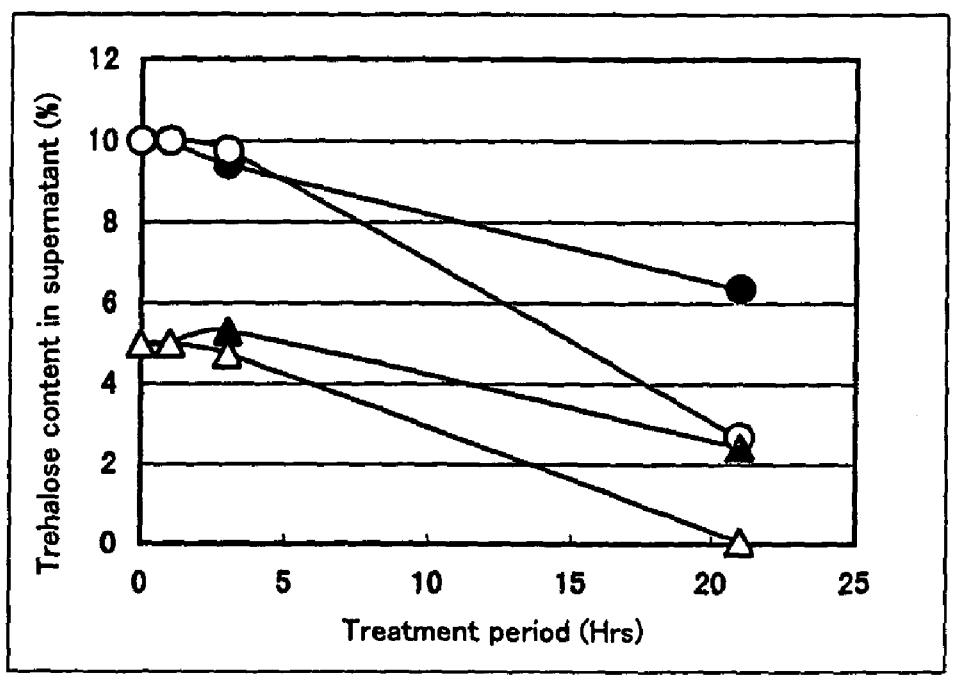
FIG. 1 is a graph showing the results obtained by soaking a yeast in trehalose solutions and monitoring changes in the trehalose contents in the supernatants.

As discussed above, dry yeasts suffer from a significant loss of activity in the course of drying. In a case of being used as starters for producing alcoholic beverages, moreover, these dry yeasts need to be acclimatized to the anaerobic conditions for alcohol fermentation. Accordingly, it has never been attempted to store yeasts recovered from the fermentation step of manufacturing alcoholic beverages as dry yeasts.

However, the present inventors focussed on the fact that an expression of a gene of α-glucoside transporter (AGT1), which transports maltose into cells, is induced in a yeast having been cultured in a medium containing maltose, or glucose and fructose as the main sugar components, and which α-glucoside transporter is known as being capable of transporting not only maltose but various α-glucosides including trehalose into yeast cells (Mol. Microbiol., 17, 1093–1107 (1995)). Thus, the present inventors assumed that a yeast recovered from the fermentation step of wort containing maltose, or glucose and fructose as the main sugar components might be able to increase intracellular trehalose content due to the incorporation of extracellular trehalose thereinto, and thus acquire resistance to drying. They further anticipated that a dry yeast having high fermentability and usable in producing alcoholic beverages having excellent flavor characteristics without a need to use a starter culture could be prepared from a yeast having a thus increased trehalose content. They furthermore anticipated that there might exist sugars or sugar alcohols capable of exerting a similar effect as trehalose.

From these points of view, dry yeasts were prepared by soaking a yeast recovered from a beer fermentation step in aqueous solutions respectively containing trehalose, various sugars and sugar alcohols so as to incorporate these sugars or sugar alcohols into the yeast cells, and then dehydrating and drying the yeast at a low temperature until the moisture content of the yeast was reduced to 8 to 12%. As a result, it was found that dry yeasts respectively having trehalose, mannitol, maltitol and xylose incorporated into their cells all exhibited favorable fermentability in practice, that these yeasts had high fermentability or activity, which was determined by measuring pH values in the cells, that beers produced by using these dry yeasts as starters showed similar fermentability to beers produced by using a recovered but not dried yeast, and that the beers produced by using the dry yeasts as starters were comparable in flavor qualities to those produced by using the recovered yeast as a starter. The present invention has been completed based on these findings.

Moreover, it has been confirmed that the effect achieved by the incorporation of a stabilizer such as trehalose can be further stabilized by, after soaking the yeast in the aqueous solution of a stabilizer, soaking the yeast again in an aqueous solution containing at least one component selected from a group consisting of glycerol, maltitol and xylitol to thereby incorporate the component into the yeast cells, prior to drying. Thus, a dry yeast having a further enhanced or stabilized fermentability can be obtained. It is considered that glycerol, etc. would lower water activity in the yeast cells and thus inhibit activities of enzymes whereby a stabilizer such as trehalose might be digested, although the present invention is not limited in any way by this supposition. In case where glycerol, maltitol and xylitol are employed for this purpose, therefore, these components will be called water activity-lowering agents hereinafter in this specification.

Accordingly, the present invention comprises:

(1) A method of producing an active dry yeast characterized by soaking a yeast, which has been anaerobically cultured in a medium containing maltose, or glucose and fructose as the major sugar sources, in an aqueous solution containing at least one stabilizer selected from a group consisting of trehalose, mannitol, maltitol and xylose to incorporate the stabilizer into the yeast cells, and then drying.

(2) A method of producing an active dry yeast as described in the above (1) characterized in that the yeast having the stabilizer incorporated thereinto is further soaked in an aqueous solution containing at least one water activity-lowering agent, selected from a group consisting of glycerol, maltitol and xylitol, to incorporate the water activity-lowering agent into the yeast cells thereby lowering the water activity in the cells and then dried.

(3) A method of producing an active dry yeast as described in the above (1) or (2) characterized in that the stabilizer is trehalose and the content of trehalose in the yeast cells is 10% or more in terms of dry weight ratio.

(4) A method of producing an active dry yeast as described in any of the above (1) to (3) wherein the medium containing maltose as the main sugar source is wort.

(5) A method of producing an active dry yeast as described in any of the above (1) to (4) characterized by using a yeast recovered from the fermentation step in manufacturing beer.

(6) An active dry yeast obtained by a production method as described in any of the above (1) to (5).

(7) A method of producing an alcoholic beverage characterized by adding an active dry yeast as described in the above (6) to a fermentation feedstock liquid.

(8) A production method as described in the above (7) wherein the alcoholic beverage is a brewed alcoholic beverage.

(9) A production method as described in the above (8) wherein the brewed alcoholic beverage is a beer.

(10) A production method as described in the above (8) wherein the alcoholic beverage is a wine.

(11) An alcoholic beverage produced by a method as described in the above (7).

(12) A brewed alcoholic beverage produced by a method as described in the above (8).

(13) A beer produced by a method as described in the above (9).

(14) A wine produced by a method as described in the above (10).

MODE FOR CARRYING OUT THE INVENTION

The term "active" as used in the expression "active dry yeast" in this specification means a state wherein the yeast not only contains vital cells at a high ratio but also sustains a favorable fermentability which is as close as possible to the fermentability of the yeast before drying, particularly in a case where it is used in producing alcoholic beverages.

The term "wort" refers to a saccharified liquid prepared from malt and containing maltose as the main sugar component to which a sugar solution containing maltose as the main sugar component is optionally added. Accordingly, the term "beer" as used in this specification includes beers, which are brewed products obtained by fermenting wort, and which may or may not be actually categorized as beer under the Liquor Tax Law. The term "fermentation feedstock liquid" refers to a fermentation liquid before the addition of a starter. In case of producing beer, it refers to the wort prior to the addition of a starter.

The yeast to be used in the method according to the present invention is a yeast which has been anaerobically cultured in a medium containing maltose, or glucose and fructose as the main sugar sources. In a case where the yeast to be used is obtained under different conditions (for example, aerobic conditions), it should be once anaerobically cultured in a medium containing maltose, or glucose and fructose as the main sugar sources before using. This is an essential requirement for producing an active dry yeast.

The yeast having been anaerobically cultured in a medium containing maltose, or glucose and fructose as the main sugar sources is not specifically restricted. It is preferable, however, to use a yeast recovered from the alcohol fermentation step in the production of alcoholic beverages such as beer, wine, whisky or sake; and it is particularly preferable to use a yeast recovered from the fermentation step in the production of beer. Although such a yeast is usually employed as the starter in the subsequent batch, it is discarded in a case where there is no subsequent schedule for producing beer using the same yeast strain. According to the present invention, such a yeast can be processed into a dry yeast and stored until it is reused as the starter in producing beer with the use of the same yeast strain.

The starting yeast is soaked in an aqueous solution containing at least one stabilizer selected from the group consisting of trehalose, mannitol, maltitol and xylose to incorporate the stabilizer into the yeast cells. Thus, a decrease in the yeast activity in the dehydration/drying step can be prevented. To soak the yeast in the stabilizer solution, it is necessary to prepare about 0.5 to 5 parts by weight (preferably from about 1 to 2 parts by weight), per part by weight of the slurry yeast recovered from a process for producing beer etc., of an aqueous solution of the stabilizer having a concentration of 5% or above (preferably from about 10 to 20%). Then the yeast is mixed with the aqueous stabilizer solution and the resultant mixture is allowed to stand at a temperature of about 5 to 30° C. (preferably about 10 to 20° C.) for 1 to 21 hours (preferably 1 to 3 hours). During this period, attempts should be made to keep anaerobic conditions as far as possible. If necessary, the mixture may be stirred.

Thus, the yeast actively incorporates the stabilizer into its cells and the stabilizer concentration in the cells is elevated to about 8 to 25% by weight (preferably about 10 to 20% by weight) on the basis of dry yeast cells. On the other hand, the stabilizer concentration in the external liquid is gradually lowered. In case where it is needed to measure the concentration of the stabilizer (for example, trehalose) incorporated into the cells, the trehalose content in the external liquid or the cells can be measured in accordance with the method as will be described in Example 1 hereinafter.

Treatment with the stabilizer in the method according to the present invention is characterized in that the yeast is soaked in the aqueous solution containing the stabilizer so as to incorporate the stabilizer into the yeast cells by taking advantage of the biological functions of the yeast. Although studies have been made of yeast strains containing much trehalose or methods of soaking a yeast in an aqueous solution containing trehalose followed by freezing, there has never been known a method wherein an external stabilizer such as trehalose is incorporated into yeast cells for producing a dry yeast.

The yeast having the thus elevated stabilizer concentration in the cells can be dehydrated and dried as such. In a preferred embodiment of the present invention, however, the yeast is further soaked in an aqueous solution containing at least one water activity-lowering agent selected from the group consisting of glycerol, maltitol and xylitol to incorporate the water activity-lowering agent into the yeast cells thereby lowering the water activity in the cells before the dehydration/drying. The water activity-lowering agent (for example, glycerol) lowers the water activity in the cells and thus prevents the stabilizer (for example, trehalose) having been incorporated into the cells from digestion by trehalase, etc. Moreover, the water activity-lowering agent prevents a decrease in the activity of the yeast during the dehydration/drying procedures.

The water activity-lowering agent is used in the form of an aqueous solution having a concentration of about 5 to 30% (preferably about 10 to 20%) in which the yeast is soaked. To soak the yeast, it is needed to prepare about 0.2 to 5 parts by weight (preferably about 0.5 to 2 parts by weight) an aqueous solution of the water activity-lowering agent such as glycerol having a concentration of about 10 to 60% (preferably about 20 to 40%) per part by weight of the semi-solid or slurry yeast which has been dehydrated by an appropriate procedure such as centrifugation, filtration or filter press. Then the yeast is mixed with the aqueous solution of the water activity-lowering agent and sufficiently suspended therein. Next, the resultant suspension is allowed to stand at a temperature of about 5 to 30° C. (preferably about 10 to 20° C.) for 0.1 to 1 hour (preferably 0.2 to 0.3 hour).

After treating with the water activity-lowering agent, the yeast is dehydrated/dried until its moisture content is lowered to about 8 to 12%. In this step, the yeast is dehydrated/dried at a low temperature (for example, 0 to 25° C., preferably 5 to 10° C.) compared with the conventional methods of producing dry yeasts. By thus controlling the temperature, a dry yeast having a high activity can be produced. The conditions except the dehydration/drying temperature can be appropriately selected in accordance with the conditions conventionally employed for producing dry yeasts. For example, dehydration can be performed by centrifugation, filtration, filter pressing, etc. The yeast thus dehydrated is granulated by extrusion and then dried in a fluidized bed dryer, a tunnel dryer or the like. Thus, the dry yeast according to the present invention can be obtained.

The active dry yeast according to the present invention may be various brewer's yeasts, for example, beer yeasts, wine yeasts, sake yeasts and whisky yeasts. Therefore, various alcoholic beverages can be produced by using the active dry yeast according to the present invention as a starter depending on the desired purpose.

The active dry yeast according to the present invention can be added as a starter to a fermentation feedstock liquid without needing the culture of the starter to thereby provide alcoholic beverages having excellent flavor. To add to the fermentation feedstock liquid, the active dry yeast may be directly poured thereinto. Alternatively, the active dry yeast may be suspended in water, or the fermentation feedstock liquid, for example, wort (in case of producing beer), and then added to the fermentation feedstock liquid.

EXAMPLES

Now, the present invention will be described in greater detail by reference to the following Examples.

Example 1

Ability to Incorporate Trehalose and Activity of Recovered Yeast 50 g of a slurry yeast recovered from the beer fermentation step (hereinafter referred to as the recovered yeast) was treated with trehalose by adding 50 g of a 10% (w/w) or 20% (w/w) aqueous trehalose solution and stirring. After mixing with the recovered yeast, the trehalose-treatment liquids respectively contained 5% (w/w) and 10% (w/w) of trehalose. The trehalose-treatment was carried out at 10° C. or 20° C. The trehalose-treatment liquids were sampled with the passage of time and each sample was centrifuged to thereby separate into cells and a supernatant. The trehalose content in the supernatant was measured by liquid chromatography with the use of a Shim-pack CLC-NH2 column (manufactured by Shimadzu Corporation). By using the wet cells, the intracellular pH value was measured by $^{31}$P-NMR in accordance with a publicly known method (European Brewery Convention 26$^{th}$ Congress, EBC;423–430 (1997)). After freeze-drying, 100 mg of the cells were weighed into an Ependorf tube, thoroughly suspended in 1 ml of sterilized water and treated at 100° C. for 30 minutes to thereby extract sugars in the cells. Then the cells were eliminated by centrifuging at 12000 rpm for 1 minute, and the trehalose content in the supernatant was measured by the above-described liquid chromatographic method. Thus, the trehalose content on the basis of the dry cell weight was measured.

Figure 2:
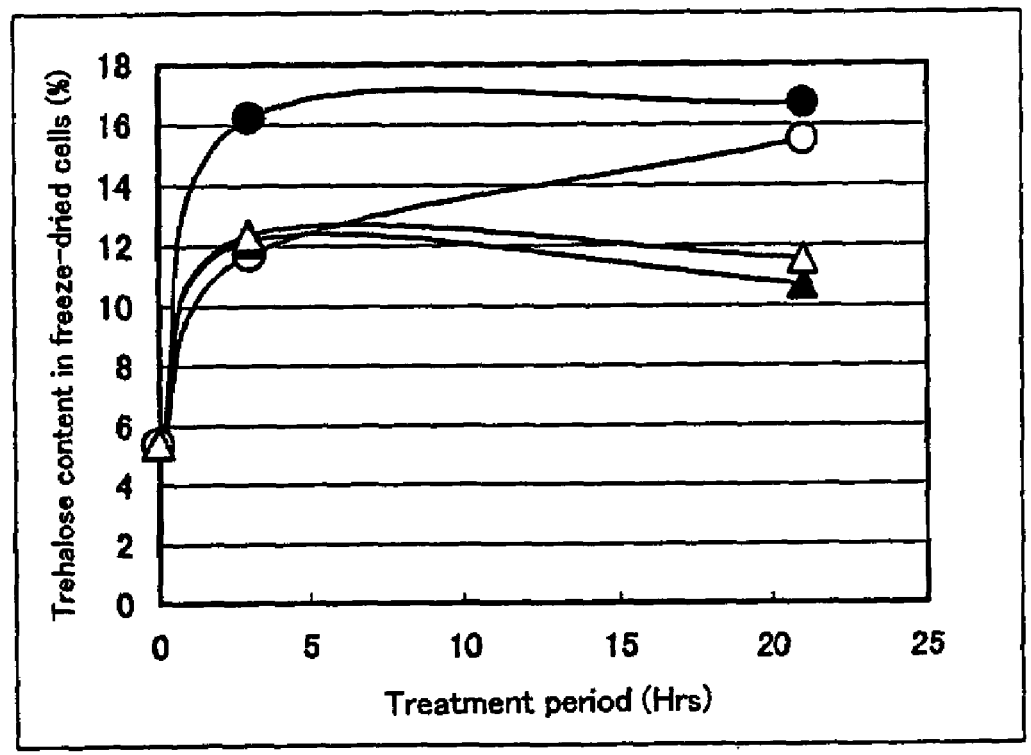
FIG. 2 is a graph showing the results obtained by monitoring changes in the intracellular trehalose contents for about 20 hours under the same conditions as in FIG. 1.

FIG. 1 shows changes in the trehalose contents in the supernatants, while FIG. 2 shows changes in the trehalose contents in the cells. At each trehalose concentration (i.e., 5% or 10%) and at each treatment temperature (i.e., 10° C. or 20° C.), the trehalose in the supernatant was continuously lowered. In the case where the treatment was carried out at a trehalose concentration of 5% and at a temperature of 20° C. for about 20 hours, the trehalose content in the supernatant became 0. On the other hand, the intracellular trehalose content attained 12% or more on the basis of the dry cell weight 3 hours after the initiation of the treatment under each of the conditions. Subsequently, no large change in the trehalose content was observed except in the case where the treatment was carried out at a trehalose concentration of 10% and at a temperature of 20° C. and thus an increase in the trehalose content was observed. Under these conditions where no large change was observed, the incorporation of trehalose and the decrease in trehalose due to the digestion into glucose and owing to the glycolytic metabolism were seemingly well balanced. In fact, it was confirmed by the $^{31}$P-NMR that intermediate metabolites in the glycolysis pathway were increased in the yeast cells having been treated with trehalose. Based on these facts, it was found out that the content of trehalose in the dry yeast cells attained 12% or more after performing the trehalose incorporation treatment for 3 hours.

Figure 3:
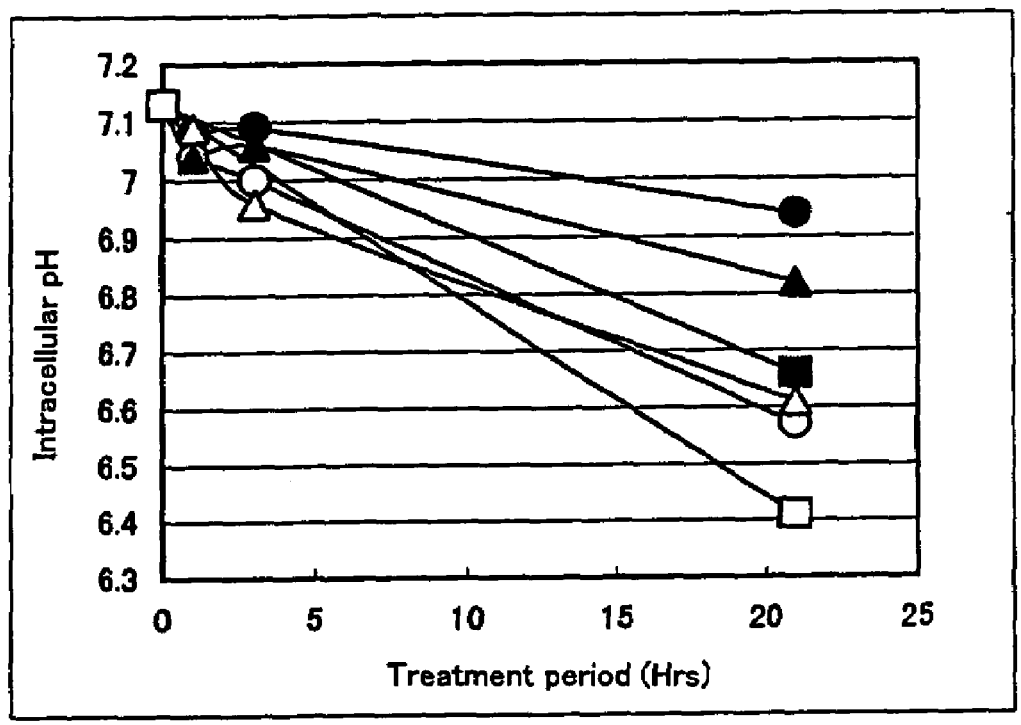
FIG. 3 is a graph showing the results obtained by monitoring the changes in the pH values in the cells for about 20 hours under the same conditions as in FIG. 1.

FIG. 3 shows changes in the intracellular pH values during the trehalose-treatments. It was found out that the yeast treated with water showed a lower intracellular pH value than the yeast treated with trehalose at the same temperature. Since JP (Kokai) Hei-8-266297 discloses that the intracellular pH value of a yeast correlates to its activity (i.e., a lower activity at the lower intracellular pH value), the above-described results indicate that a decrease in the yeast activity can be more efficiently prevented by the trehalose-treatment than by the water-treatment.

Example 2

Improvement in Resistance to Drying by the Incorporation of Trehalose 50 g of a 20% aqueous solution of trehalose was added to 50 g of the recovered yeast and the resultant mixture was stirred at 20° C. for 3 hours to thereby incorporate the trehalose into the yeast cells. Then the yeast having trehalose thus incorporated was filtered under suction on a filter paper No.2 with the use of a Nutsche filter. The obtained yeast was then passed through a 14-mesh sieve and dried in a thermostat at 30° C. for about 20 hours to give a dry yeast. 0.1 g of this dry yeast was suspended and reconstituted in 1 ml of distilled water at room temperature. Then the mortality of the yeast was measured by the Methylene Blue staining method. Since dead cells could not reduce Methylene Blue, the cells stained with Methylene Blue were regarded as dead cells. Thus, the Methylene Blue staining ratio could be referred to as the mortality. As FIG. 1 shows, in a case where a dry yeast was prepared by the above-described method by using the recovered yeast without treating with trehalose, about 90% of the cells died due to the drying procedure. Thus, trehalose was incorporated as in Example 1 and then the yeast was dried.

Table 1 shows the mortalities before drying and after reconstituting the dry yeast with water as described above. In case where 5% of trehalose was incorporated at a temperature of 10° C., the ratio of the dead cells was lowered to about 60% by treating with trehalose for 1 or 3 hours. In a case where the treatment was carried out for 21 hours and then the cells were dried and reconstituted with water, about 90% of the cells died. At the treatment temperature of 20° C., a decrease in the mortality could be confirmed exclusively in the case where the trehalose treatment was carried out for 1 hour and then the yeast was dried and reconstituted with water. At the concentration of the trehalose to be incorporated of 10%, the ratio of the dead cells was lowered to 60 to 70% after treating for 1 to 3 hours even in the case where the treatment temperature was 10° C. or 20° C. Based on these results, it was found out that the resistance to drying could be imparted to the recovered yeast by treating with 5% or 10% of trehalose for 3 hours followed by drying and reconstitution with water.

TABLE 1

Methylene Blue-staining ratio of yeast under various treatment conditions

| Treating time (Hrs) | | Untreated recovered yeast | Suspended in water 10° C. | Suspended in water 20° C. | Treated with 5% trehalose 10° C. | Treated with 5% trehalose 20° C. | Treated with 10% trehalose 10° C. | Treated with 10% trehalose 20° C. |
|---|---|---|---|---|---|---|---|---|
| Before drying | 1 | 7.69 | 8.17 | 7.96 | 8.97 | 6.58 | 6.36 | 8.26 |
| | 3 | | 7.97 | 10.44 | 8.45 | 7.51 | 8.67 | 9.24 |
| | 21 | | 8.33 | 20.45 | 11.88 | 16.44 | 17.68 | 8.90 |
| Immediately after re-constitution with water | 1 | 88.89 | | | 63.72 | 64.95 | 69.51 | 62.15 |
| | 3 | | | | 63.40 | 84.17 | 64.95 | 62.04 |
| | 21 | | | | 90.11 | 92.47 | 79.33 | 87.43 |

Each value in the above table indicates the staining ratio with Methylene Blue.

Example 3

Figure 4:
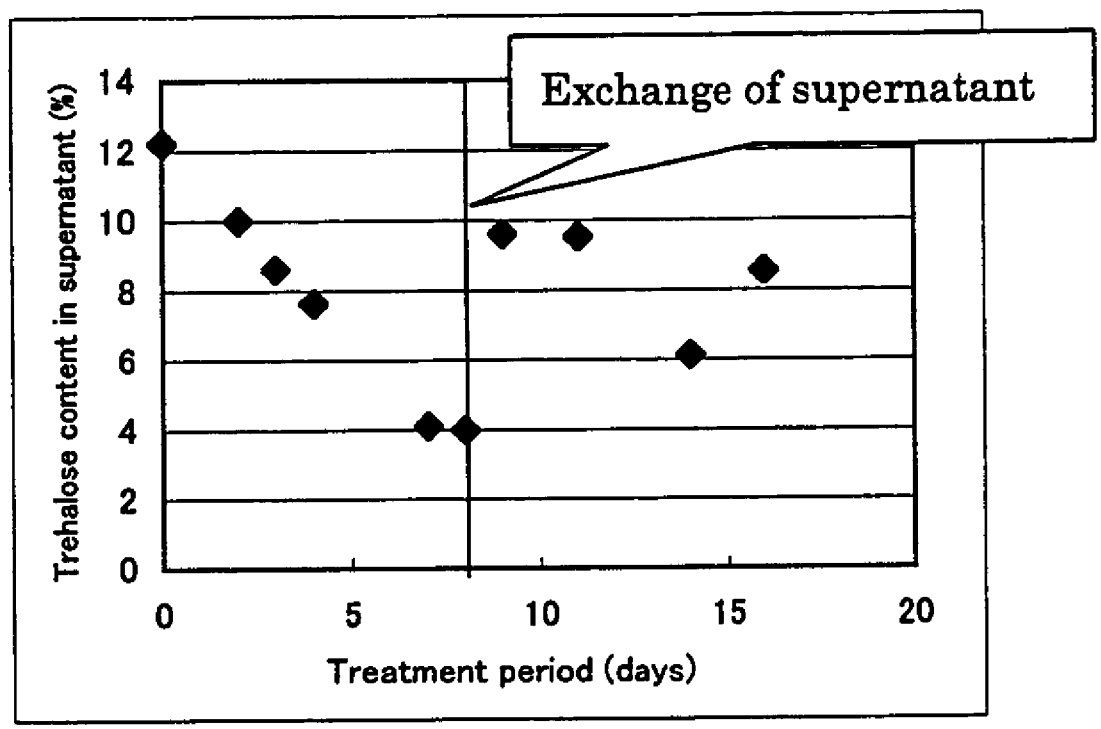
FIG. 4 is a graph showing the results obtained by treating a yeast with trehalose for 8 days, collecting the cells, treating the cells with trehalose again and then monitoring the changes in the trehalose contents in the supernatants.

Improvement in Storage Properties by the Incorporation of Trehalose 250 g of the recovered yeast was suspended in the same weight of purified water or a 20% aqueous solution of trehalose and then maintained at 5° C. for about 2 weeks. The trehalose contents in the supernatant and in the cells and the intracellular pH values were monitored with the passage of time as in Example 1. When the trehalose content in the supernatant was measured by the method described in Example 1, the trehalose content was lowered from 10% at the initiation of the treatment to 4% on the day 7 due to the incorporation into the yeast, as FIG. 4 shows. Since the trehalose content in the supernatant was lowered to 2% on the day 8 after the initiation of the treatment, the yeast under the trehalose-treatment was separated by centrifugation and suspended by adding a 20% aqueous trehalose solution again. Then, the trehalose-treatment was continued. A portion of the yeast under the trehalose-treatment or the water-treatment was sampled 4 and 8 days after the initiation of respective treatments. Then each sample was added to 2L of a wort having a Brix of 14% so as to give a viable count of 28×10$^6$ cells/ml. Then a fermentation test was carried out at 15° C.

Figure 5:
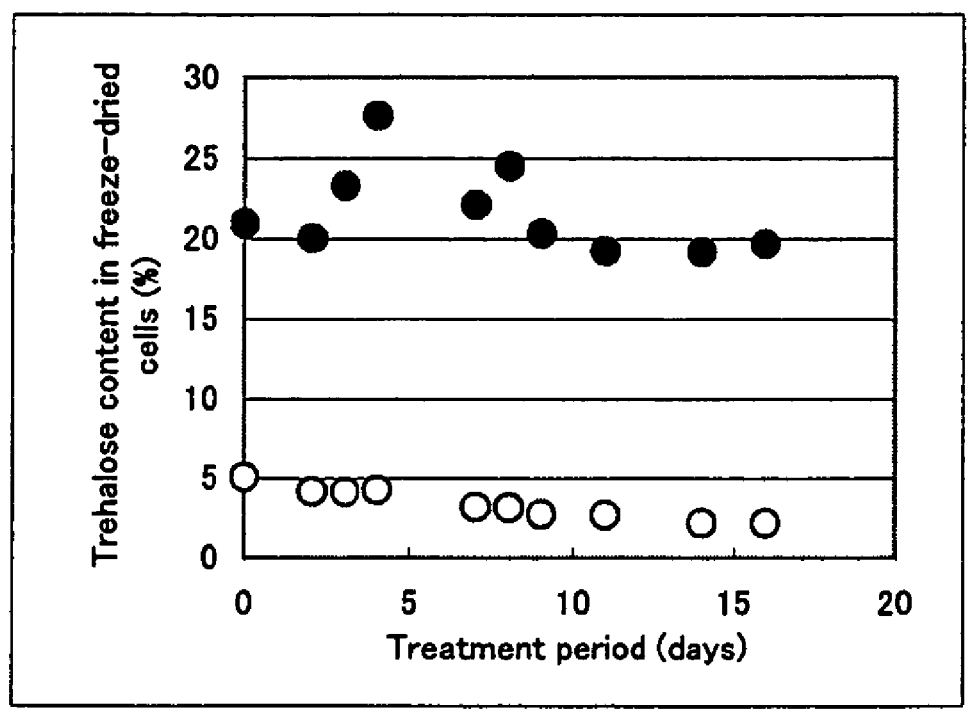
FIG. 5 is a graph showing the results obtained by monitoring the changes in the trehalose contents in freeze-dried cells on each test day under the same conditions as in FIG. 4.
Figure 6:
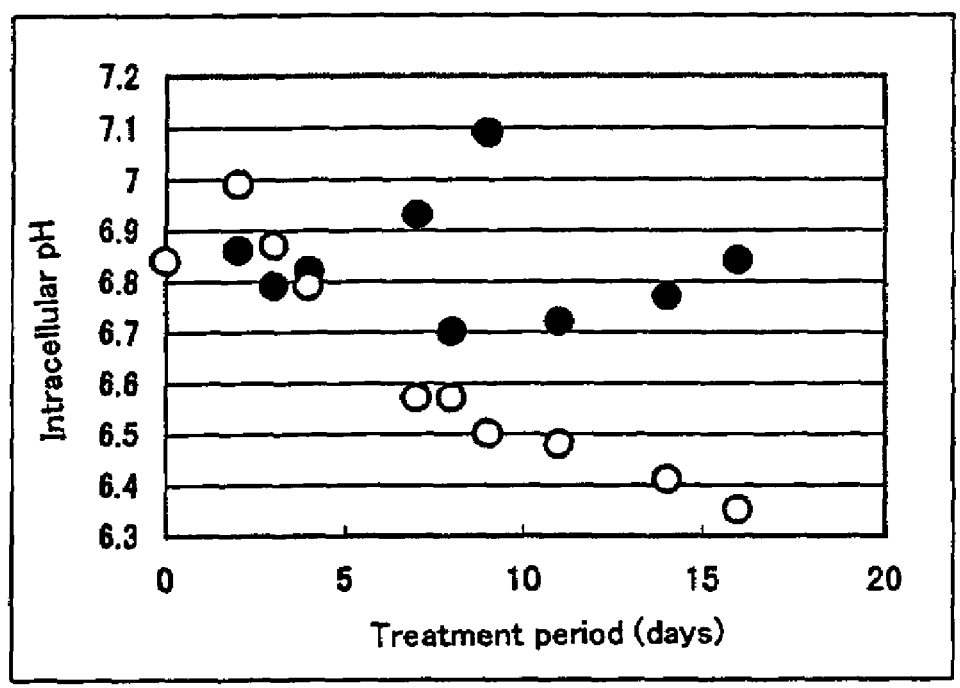
FIG. 6 is a graph showing the results obtained by monitoring the changes in the pH values in the yeast cells under the same conditions as in FIG. 4.
Figure 7:
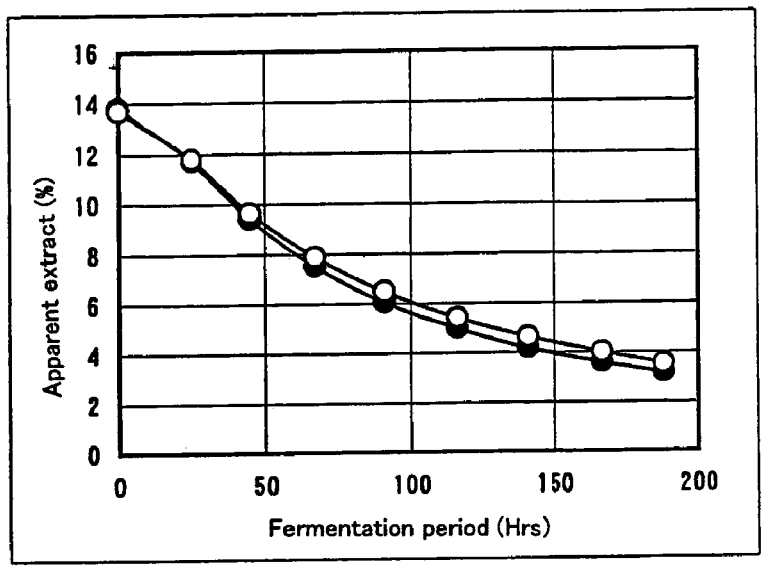
FIG. 7 shows the results of a 2L-scaled fermentation test using a yeast having been treated with trehalose for 4 days under the same conditions as in FIG. 4, wherein FIG. 7-A is a graph showing changes in the apparent extract while FIG. 7-B is a graph showing changes in viable count.
Figure 7:
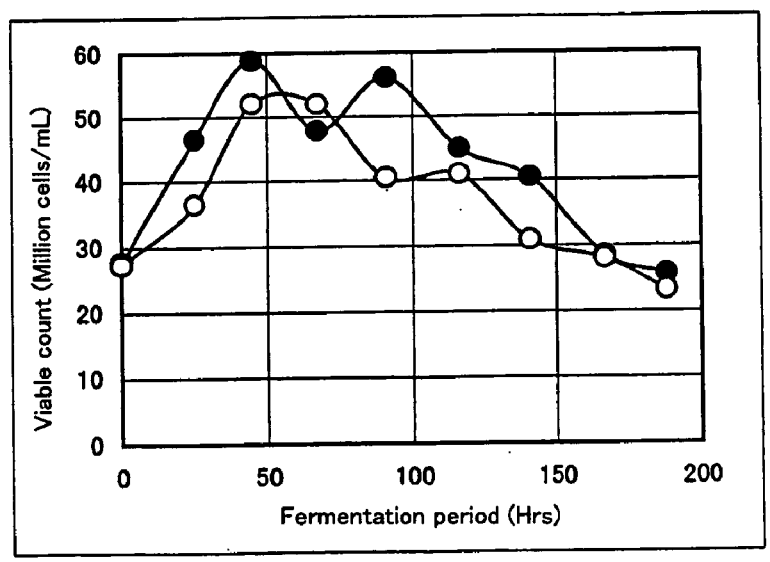
Figure 8:
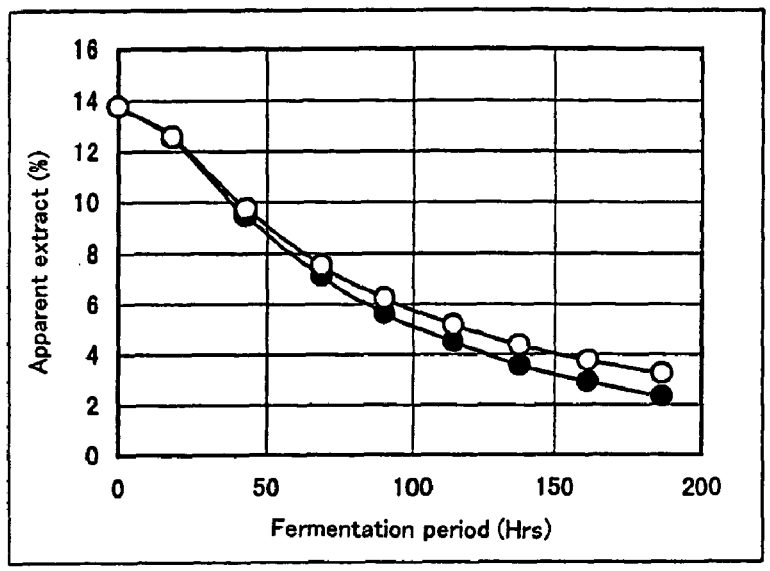
FIG. 8 shows the results of a 2L-scaled fermentation test using a yeast having been treated with trehalose for 8 days under the same conditions as in FIG. 4, wherein FIG. 8-A is a graph showing changes in the apparent extract while FIG. 8-B is a graph showing changes in viable count.
Figure 8:
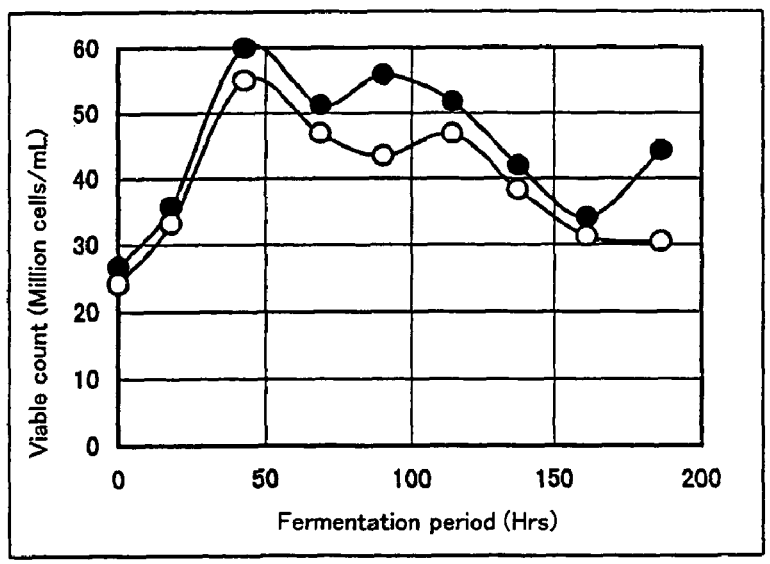

As FIG. 5 shows, the trehalose content in the cells attained 20% on the basis of dry cells by the day 3 after the initiation of the treatment, and sustained the level of 20% or above until the day 16. As FIG. 6 shows, the intracellular pH value of the yeast under the water-treatment was lowered from 6.84 at the initiation of the treatment to 6.35 on the day 16. In contrast thereto, no change was observed in the case of the trehalose-treatment. As the results of the 2L-scaled fermentation test, the recovered yeast under the trehalose-treatment was superior to the recovered yeast under the water-treatment in fermentation performance from the viewpoints of fermentability (FIGS. 7-A and 8-A) and yeast proliferation (FIGS. 7-B and 8-B), as shown in FIGS. 7 and 8. As discussed above, it has been found out that the fermentability and activity of the recovered yeast can be elevated by the trehalose-treatment compared with the water-treatment. Namely, it has been confirmed that the storage properties of the yeast can be improved by the trehalose-treatment.

Example 4

Examination on Drying Temperature

As the results of Example 2 show, the trehalose-treatment alone could not sufficiently lower the mortality after the drying/rehydration with water. Thus, it was attempted to lower the drying temperature. The yeast was subjected to the trehalose-treatment as in Example 2 and dried at 30° C. or 5° C. and then the mortality after the rehydration with water was measured by the Methylene Blue staining method. As Table 2 shows, it was found out that the survival ratio could be elevated by the trehalose-treatment and by lowering the drying temperature.

TABLE 2

Examination on drying temperature

| | No trehalose-treatment | Trehalose-treatment |
|---|---|---|
| Mortality (%) after drying at 30° C. | 83.6% | 73.4% |
| Mortality (%) after drying at 50° C. | 64.8% | 58.0% |

Example 5

Effect of Glycerol-treatment

As Example 4 shows, the trehalose-treatment and drying at 5° C. were still insufficient for achieving a satisfactory survival ratio after the drying/rehydration with water. Therefore, the yeast was treated with glycerol to lower the water activity in the yeast cells. After thus inhibiting the activities of various enzymes such as a trehalose hydrolyzing enzyme and enzymes in the glycolysis pathway, the dehydration and drying were carried out. 50 g of the slurry yeast recovered from the beer fermentation step was treated with trehalose as in Example 2 and then centrifuged. Next, the yeast cells were suspended in 50 g of 300 g/L aqueous glycerol solution and maintained at room temperature for 15 minutes. Subsequently, the yeast was filtered under suction on a filter paper No.2 as in Example 2. The obtained yeast was passed through a 14-mesh sieve and dried in a thermostat at 5° C. for about 20 hours. The dry yeast thus obtained was reconstituted with water as in Example 2 and stained with Methylene Blue to measure the mortality of the yeast.

TABLE 3

Effect of glycerol-treatment on Methylene Blue-staining ratio

| | No glycerol-treatment | Glycerol-treatment |
|---|---|---|
| Before drying | 13.1% | 95.8% |
| After drying/reconstitution with water | 36.9% | 18.3% |

Each value in the table stands for a Methylene Blue-staining ratio.

As Table 3 shows, the yeast immediately after treated with glycerol could not reduce Methylene Blue since the activity of the Methylene Blue reductase was inhibited by glycerol and thus almost all of the cells were stained. However, when the yeast was dehydrated and dried and then the thus obtained dry yeast was rehydrated with water and stained with Methylene Blue, the Methylene Blue-staining ratio (i.e., the mortality) of the yeast was largely lowered as the enzymatic activity was restored by the rehydration with water. It has been thus confirmed that the glycerol-treatment following the trehalose-treatment is remarkably effective in elevating the survival ratio of the yeast after the drying/reconstitution with water.

Example 6

Results of 70L-scaled Brewing Test 70L of a wort with a Brix of 14% was prepared. Then the recovered yeast, the active dry yeast prepared as in Example 5 and a marketed dry yeast for brewing beer (Saflager S-189 manufactured by Lasaffre) were added thereto so as to give each a viable count of $28 \times 10^6$ cells/ml. During fermenting at 15° C., the fermentability was monitored with the passage of time. When the fermentation was completed, the contents of esters and sulfur dioxide were measured, and each beer product was evaluated organoleptically.

Figure 9:
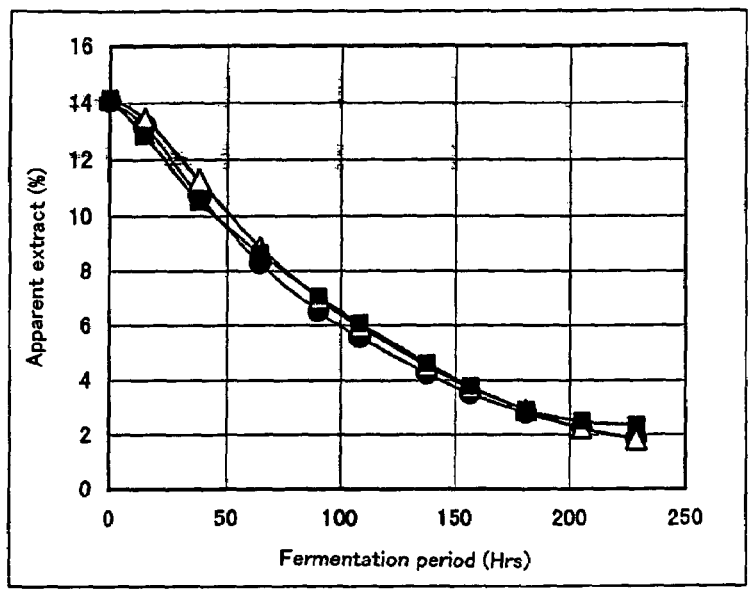
FIG. 9 is a graph showing changes in the apparent extract in a 70L-scaled fermentation test using the dry yeast according to the present invention produced in Example 5.

As FIG. 9 shows, no large difference in the degree of fermentation evaluated based on the decrease in extract consumption (i.e., the apparent extract) was observed among these three starters. Table 4 shows the contents of esters and sulfur dioxide at the point of completion of the fermentation.

TABLE 4

Contents of esters and sulfur dioxide at the point of completion of the fermentation

|  | Ethyl acetate | Isoamyl acetate | Sulfur dioxide |
|---|---|---|---|
| Recovered yeast | 27.53 | 2.20 | 4.16 |
| Dry yeast | 24.94 | 1.98 | 4.22 |
| Marketed dry yeast | 22.16 | 0.29 | 1.92 |

Each value in the table is expressed in mg/L.

In a case of using the marketed dry yeast as the starter, the esters and sulfur dioxide were formed in small amounts compared with the case of using the recovered yeast as the starter. In the case of the fermentation with the use of the active dry yeast produced by the method according to the present invention as the starter, the amounts of the esters and sulfur dioxide thus formed were comparable to the case of using the recovered yeast. As Table 5 shows, the alcoholic beverage brewed by using the marketed dry yeast was inferior in flavor to the alcoholic beverage obtained by using the recovered yeast, while the alcoholic beverage produced by using the active dry yeast as the starter showed a flavor comparable to the alcoholic beverage obtained by using the recovered yeast.

TABLE 5

Results of organoleptic evaluation

| Recovered yeast | Dry yeast | Marketed dry yeast |
|---|---|---|
| Normal | No difference from recovered yeast | Showing different smell |
| Usual evaluation | Normal evaluation | Poor evaluation |

Example 7

Examination on Glycerol-treatment Concentration

Although a 300 g/L aqueous glycerol concentration was used in Example 5, it was attempted whether or not similar results could be obtained by using aqueous glycerol solutions of lower concentrations.

To 50 g of the slurry yeast recovered from the beer fermentation step, 50 g of an aqueous trehalose solution of about 20% in concentration was added. After stirring at 20° C. for 3 hours, the yeast was separated by centrifuging and suspended in 50 g portions of aqueous glycerol solutions of 300 g/L, 200 g/L, 150 g/L and 100 g/L in concentration. After maintaining at room temperature for 15 minutes, each mixture was filtered under suction on a filter paper No. 2 as in Example 2. The yeast thus obtained was passed through a 14-mesh sieve and dried in a thermostat at 5° C. for about 20 hours. The dry yeast thus obtained was reconstituted with water immediately after the completion of the preparation and after storing at 25° C. for 8 days. Then the Methylene Blue-staining ratios were measured as in Example 2.

TABLE 6

Effect of changes in glycerol-treatment concentration on Methylene Blue-staining ratio (expressed in %)

|  | 300 g/L | 200 g/L | 150 g/L | 100 g/L |
|---|---|---|---|---|
| Before drying | 99.6 | 97.8 | 66.7 | 20.8 |
| Immediately after drying/reconstitution with water | 26.2 | 26.3 | 23.7 | 30.8 |
| After reconstitution with water after drying and storing at 25° C. for 8 days | 48.5 | 40.2 | 62.3 | 59.8 |

Although similar results could be obtained by using the aqueous glycerol solutions of 200 g/L and 300 g/L, the Methylene Blue-staining ratios in the cases of the aqueous glycerol solutions at 150 g/L and 100 g/L were not so high as at 300 g/L. When the yeast was reconstituted with water immediately after drying and then stained with Methylene Blue, no large difference in Methylene Blue-staining ratio was observed among the aqueous glycerol solutions at various concentrations. When the yeast was dried, stored at 25° C. for 8 days and then reconstituted with water, the Methylene Blue-staining ratios at the glycerol concentrations of 150 g/L and 100 g/L were higher than at 300 g/L, which indicates that the former yeast samples were inferior in qualities to the latter.

Example 8

Examination on Substitutes for Trehalose

As Example 5 shows, it has been confirmed that the glycerol-treatment following the trehalose-treatment is remarkably effective in elevating the survival ratio of the yeast after drying/reconstitution with water. Then, an examination was made whether or not similar effects could be obtained by using sugars or sugar alcohols other than trehalose.

To 50 g of the slurry yeast recovered from the beer fermentation step, 50 g portions of aqueous solutions (concentration: about 20%) of various sugars and sugar alcohols were added respectively. After stirring at 20° C. for 3 hours, the yeast was centrifuged, suspended in 50 g of a 300 g/L aqueous glycerol solution and maintained at room temperature for 15 minutes. Subsequently, the yeast was filtered under suction on a filter paper No.2 as in Example 2. The obtained yeast was passed through a 14-mesh sieve and dried in a thermostat at 5° C. for about 20 hours. The dry yeast thus obtained was reconstituted with water as in Example 2 and stained with Methylene Blue to measure the mortality of the yeast.

TABLE 7

Effects of various sugars and sugar alcohols employed as substitute for trehalose in producing dry yeast on Methylene Blue-staining ratios after reconstitution with water

| Sugar/sugar alcohol | Trehalose | Xylose | Galactose | Glucose | Lactose | Mannose | Fructose |
|---|---|---|---|---|---|---|---|
| Methylene Blue-staining ratio (%) | 32.2 | 37.7 | 40.6 | 43.6 | 38.6 | 40.6 | 51.1 |

| Sugar/sugar alcohol | Xylobiose | Cellobiose | Maltose | Sucrose | Mannitol | Xylitol | Sorbitol | Maltitol |
|---|---|---|---|---|---|---|---|---|
| Methylene Blue-staining ratio (%) | 46.5 | 54.8 | 56.4 | 51.9 | 37.1 | 41.6 | 41.8 | 29.7 |

As the above tables show, it has been confirmed that xylose, mannitol, maltitol, etc. are effective in elevating the survival ratio of the dry yeast after the reconstitution with water similar to trehalose.

Example 9

Examination on Substitutes for Glycerol

As Example 5 shows, it has been confirmed that the glycerol-treatment following the trehalose-treatment is remarkably effective in elevating the survival ratio of the yeast after drying/reconstitution with water. Then, examination was made as to whether or not similar effects could be obtained by using sugar alcohols other than glycerol.

To 50 g of the slurry yeast recovered from the beer fermentation step, 50 g of an aqueous trehalose solution (concentration: about 20%) was added. After stirring at 20° C. for 3 hours, the yeast was centrifuged, suspended in 50 g portions of 300 g/L aqueous solutions of various sugar alcohols and maintained at room temperature for 15 minutes. Subsequently, the yeast was filtered under suction on a filter paper No.2 as in Example 2. The obtained yeast was passed through a 14-mesh sieve and dried in a thermostat at 5° C. for about 20 hours. The dry yeast thus obtained was reconstituted with water as in Example 2 and stained with Methylene Blue to measure the mortality of the yeast.

TABLE 8

Effects of various sugar alcohols employed as substitute for glycerol in producing dry yeast on Methylene Blue-staining ratios after reconstitution with water

| Sugar alcohol | Glycerol | Maltitol | Mannitol | Xylitol | Sorbitol |
|---|---|---|---|---|---|
| Methylene Blue-staining ratio (%) | 24.4 | 30.1 | 47.5 | 30.4 | 41.2 |

As Table 8 shows, it has been confirmed that maltitol, xylitol, etc. are effective in elevating the survival ratio of the yeast after the reconstitution with water similar to glycerol.

Example 10

Results of Examination on Drying Conditions

In Example 4, it is shown that, as the results of the examination on the drying temperature of the yeast after the trehalose-treatment, the survival ratio of the yeast could be elevated by lowering the drying temperature to 5° C. In this Example, the temperature for drying the yeast after the trehalose-treatment and the glycerol-treatment was discussed in greater detail. As it was assumed that the survival ratio of the yeast might be elevated by drying more quickly even at 30° C., drying in a fluidized bed dryer was also examined.

To 50 g of the slurry yeast recovered from the beer fermentation step, 50 g of an aqueous trehalose solution (concentration: about 20%) was added. After stirring at 20° C. for 3 hours, the yeast was centrifuged, suspended in 50 g of an about 300 g/L aqueous glycerol solution and maintained at room temperature for 15 minutes. Subsequently, the yeast was filtered under suction on a filter paper No.2 as in Example 2. The obtained yeast was passed through a 14-mesh sieve and dried in a thermostat at 5° C. to 30° C. for about 20 hours. Alternatively, the yeast was dried by using a fluidized bed dryer at 30° C. for 1 hour. Each of the dry yeast thus obtained was rehydrated with water as in Example 2 and stained with Methylene Blue to measure the mortality of the yeast.

TABLE 9

Effects of drying conditions on Methylene Blue-staining ratios of dry yeast after reconstitution with water

| Drying method | Thermostat | | | | Fluidized bed dryer |
|---|---|---|---|---|---|
| Drying temp. (° C.) | 5 | 10 | 20 | 30 | 30 |
| Methylene Blue-staining ratio (%) | 42.0 | 36.3 | 42.2 | 69.8 | 38.6 |

As the above table shows, the Methylene Blue-staining ratios after the reconstitution with water were almost the same regardless of the temperature in case of using the thermostat, so long as the temperature was 20° C. or lower. In case of 30° C. alone, about 70% of the yeast cells died. In a case of drying more quickly with the use of the fluidized bed dryer, in contrast, the survival ratio of the yeast was elevated even though at 30° C.

Example 11

Preparation of Dry Wine Yeast and Results of Brewing Test

By using a wine fermentation yeast, it has been confirmed that the method of producing a dry yeast according to the present invention is applicable to processes for producing alcoholic beverages other than beer.

Figure 10:
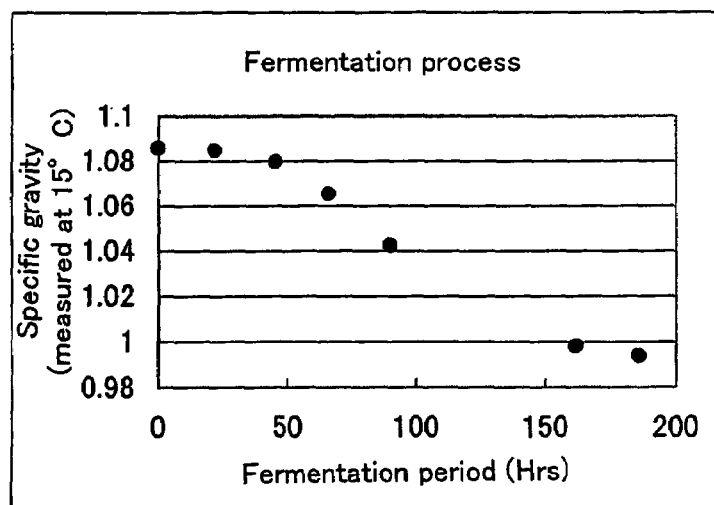
FIG. 10 provides a graph which shows the fermentability of the dry wine yeast prepared in accordance with the method of the present invention.

A grape juice was diluted so as to give a specific gravity (measured at 15° C.) of 1.0857. Then a wine fermentation yeast having been cultured separately was added thereto. Grape juice contains glucose and fructose as the main sugar components in almost the same amounts (*Hakko Handbook*, p. 549, Kyoritsu Shuppan (2001)). After fermenting at 20° C. for 3 days, the yeast was separated from the fermented liquid by centrifugation. To 50 g of the slurry yeast thus recovered, 50 g of an about 20% aqueous trehalose solution was added. After fermenting at 20° C. for 3 hours, the yeast was centrifuged, suspended in 50 g of an aqueous glycerol solution (concentration: about 150 g/L) and then maintained at room temperature for 15 minutes. Subsequently, the yeast was filtered under suction on a filter paper No.2 as in Example 2. The obtained yeast was passed through a 14-mesh sieve and dried in a thermostat at 5° C. for about 20 hours. The thus obtained dry yeast was rehydrated with water as in Example 2 and stained with Methylene Blue to measure the mortality of the yeast. As a result, the survival ratio of the yeast was 70.15%. The reconstituted dry yeast was added to 1.5L of a diluted grape juice (specific gravity: 1.0857) and fermentation was carried out at 20° C. Thus the fermentation proceeded in a favorable manner (see FIG. 10).

Effects of the Invention

The present invention provides a technique whereby a yeast for producing alcoholic beverages can be stored over a long time while sustaining a high viable cell ratio and a high fermentability. Although it has been a practice to employ yeasts recovered from fermentation step for producing alcoholic beverages as starters in the subsequent production step, vital yeasts are denatured quickly and thus the fermentability is damaged. Therefore, these recovered yeasts can remain usable only for a week at the longest. According to the present invention, the storage properties of these yeasts which are liable to undergo denaturation can be remarkably improved and thus the productivity in plants for manufacturing alcoholic beverages can be elevated in practice. That is to say, the present invention makes it possible to omit the equipment and steps for the so-called starter development required in the conventional art, wherein a seed yeast is once grown by aerobic culture and then acclimatized to anaerobic conditions to thereby prepare a yeast for producing alcoholic beverages, and thus much labor, time and cost for producing alcoholic beverages can be saved.

The invention claimed is:

1. A method of producing an active dry yeast by comprising:
   soaking a yeast, which has been anaerobically cultured in a medium containing maltose, or glucose and fructose as the major sugar sources, in an aqueous solution containing at least one stabilizer selected from the group consisting of trehalose, mannitol, maltitol and xylose to incorporate the stabilizer into the yeast cells;
   soaking the yeast in an agueous solution containing at least one water activity-lowering agent selected from the group consisting of glycerol, maltitol and xylitol to incorporate the water activity-lowering agent into the yeast cells thereby to lower the water activity in the cells; and
   drying the yeast.

2. A method of producing an active dry yeast according to claim 1 characterized in that the stabilizer is trehalose and the content of trehalose in the yeast cells is 10% or more in terms of dry weight ratio.

3. A method of producing an active dry yeast according to claim 1 wherein the medium containing maltose as the main sugar source is wort.

4. A method of producing an active dry yeast according to claim 1 characterized by using a yeast recovered from the fermentation step in manufacturing beer.

5. An active dry yeast obtained by a production method according to claim 1.

6. A method of producing an alcoholic beverage characterized by adding an active dry yeast according to claim 5 to a fermentation feedstock liquid.

7. A production method according to claim 6 wherein the alcoholic beverage is a brewed alcoholic beverage.

8. A production method according to claim 7 wherein the brewed alcoholic beverage is a beer.

9. A production method according to claim 7 wherein the alcoholic beverage is a wine.

10. An alcoholic beverage produced by a method according to claim 6.

11. A brewed alcoholic beverage produced by a method according to claim 7.

12. A beer produced by a method according to claim 8.

13. A wine produced by a method according to claim 9.

* * * * *